United States Patent [19]

Thoms et al.

[11] Patent Number: 5,448,902
[45] Date of Patent: Sep. 12, 1995

[54] METHOD FOR THE AUTOMATIC ITERATIVE PROCESS OPTIMIZATION OF DRAWING PROCESSED IN PRESSES

[75] Inventors: Volker Thoms, Calw-Hirsau; Mathias Liewald, Stuttgart; Stephanus Faller, Renningen; Wilfried Reimche, Wunstorf; Dieter Stegemann, Gehrden 1, all of Germany

[73] Assignee: Mercedes-Benz AG, Stuttgart, Germany

[21] Appl. No.: 166,990

[22] Filed: Dec. 16, 1993

[30] Foreign Application Priority Data

Dec. 16, 1992 [DE] Germany ............... 42 42 442.9

[51] Int. Cl.$^6$ ................................................ B21D 22/22
[52] U.S. Cl. ............................................ 72/31; 72/41; 72/350
[58] Field of Search ............ 72/1, 3, 6, 31, 347, 72/350, 351, 41

[56] References Cited

U.S. PATENT DOCUMENTS

| 3,444,390 | 5/1969 | Breidenbach et al. ............ 72/31 |
| 4,023,044 | 5/1977 | Miller et al. . | |
| 4,745,792 | 5/1988 | Story et al. .................... 72/351 |
| 4,939,918 | 7/1990 | Schoch ............................ 72/20 |

FOREIGN PATENT DOCUMENTS

| 0023092A1 | 1/1981 | European Pat. Off. . | |
| 3938854A1 | 5/1990 | Germany . | |
| 3939854 | 5/1990 | Germany . | |
| 42335 | 2/1993 | Japan ............................. 72/31 |

OTHER PUBLICATIONS

F. J. Neff, "CNC and DNC operation in hydraulic presses"; Werkstatt und Betried (Workshop and Plant), 119 (1986) 11, pp. 947–949.

D. Bauer et al., "Computer-supported blank-holding pressure optimizes deep drawing"; Bleche-Baender-Rohre (Sheet Metal, Strip Metal, Pipes) 5–1990 pp. 50–54.

DE-Z Industrie-Anzeiger 17/1991, pp. 40–44.

*Primary Examiner*—Lowell A. Larson
*Attorney, Agent, or Firm*—Evenson McKeown Edwards & Lenahan

[57] ABSTRACT

The invention relates to a method for the iterative process optimization of drawing processes, occurring in timed sequence, in drawing presses. The clamping force which can be set at the blank holder is reduced in the case of fractures or increased in the case of part folding or maintained at the same level in the case of acceptable parts. In order to be able to detect the drawn part quality with respect to the criteria of "fractures", "acceptable" or "folding" automatically during each working cycle the normal variation of the drawing sound is determined by means of a sound emission analysis of the structure-borne sound caused by the drawn part during the drawing process in the drawing tool, and from this a characteristic level course from periodic to stochastic sound components is determined. During the production of the drawn parts, the structure-borne sound signal is examined in each case with regard to the simultaneous occurrence of abnormal amplitude discontinuities in a wide frequency spectrum and, if appropriate, it is concluded that there are "fractures". Furthermore, the structure-borne sound signal is examined in each case with regard to the temporal level course from periodic to stochastic sound components and, if appropriate, it is concluded that there are "folds".

19 Claims, 4 Drawing Sheets

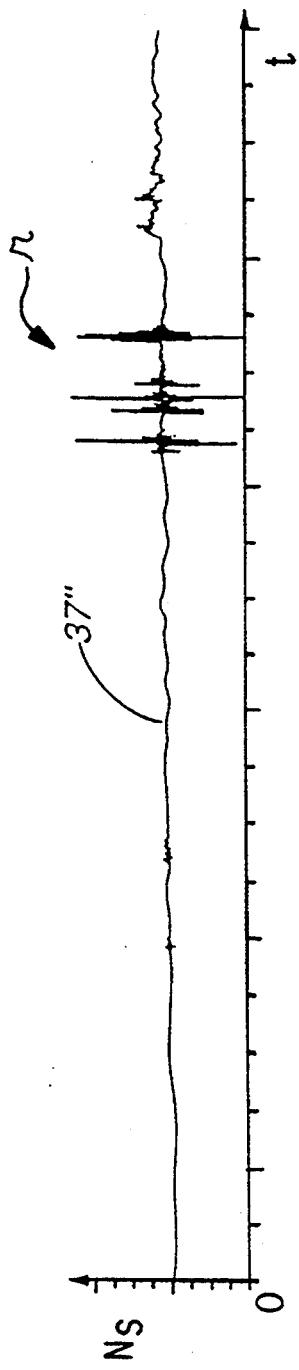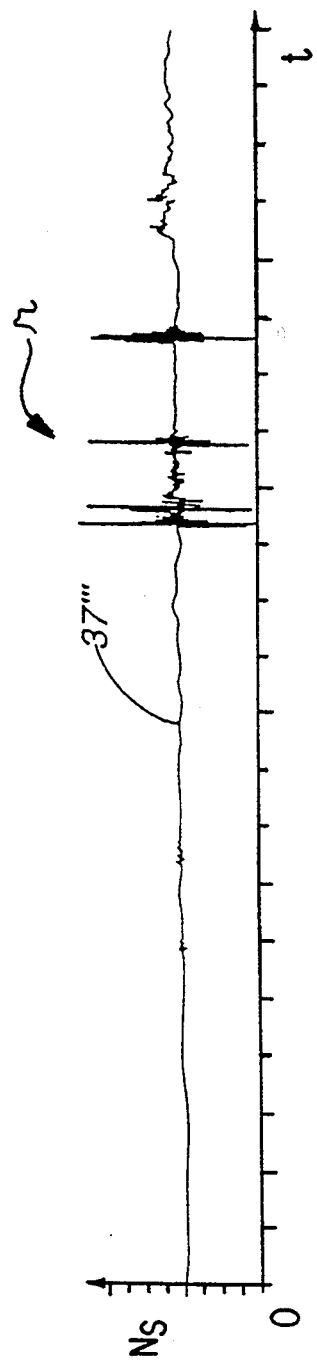
FIG. 3c
FIG. 3d

METHOD FOR THE AUTOMATIC ITERATIVE PROCESS OPTIMIZATION OF DRAWING PROCESSED IN PRESSES

BACKGROUND AND SUMMARY OF THE INVENTION

The invention is based on a method for operating drawing presses which in each case produce a drawn part during each working cycle, in each case one blank being inserted during each working cycle into the drawing tool of the drawing press, which tool consists of die, punch and blank holder and being clamped in by the blank holder at the edge with a specific clamping force and the drawn part being subsequently drawn between die and punch. Such methods are generally known, for example, from the customary practice in pressing plants.

In hand-fed drawing presses the drawing process, which occurs in a timed sequence, is corrected on the basis of a continuous visual inspection of the drawn parts by the operating personnel and of an individual manual intervention in the adjustment of the blankholding force. This is therefore a case of an adjustment process in which the human being is included as an essential, process-determining element. Apart from the monotony associated with this system and the required constant attentiveness and responsibility of the operating personnel, drawn part errors resulting from an inaccurate or incorrect adjustment of the blank-holding force are often not promptly detected. Thus, despite a constant monitoring of the drawing processes, faulty drawn parts leave the drawing press and adversely affect the productivity of the drawing press. In automatically fed presses or in pressing trains, only random sample-like visual inspection is carried out so that, particularly in modern pressing plants, there is a greater risk of rejected parts than in plants which still have complete manual operation.

In an article by F. -J. Neff, "CNC and DNC operation in hydraulic presses" in the publication Werkstatt und Betrieb (Workshop and Plant), 119 (1986) 11, pages 947 to 949, the author reports on a system for automatic quality inspection in pressing plants with appropriately developed hardware and software for a largely optimized press operation. Displacement sensors and pressure sensors for slides and die cushions are integrated into the presses. As a result, the stroke/slide force curve for each individual workpiece can be measured and also displayed with a monitor. This actual-value curve can be compared for each individual workpiece with a workpiece specific reference course. At the start of production, the reference course is produced or empirically determined for a specific workpiece to be manufactured and the data are stored; in fact, for example the stroke/slide force curve of the first fault-free drawn part can be used as a reference course. By means of the prescribed procedure and other measures not reproduced here, rapid refitting of a press to other workpieces and a monitored, i.e. failure-free press operation, or press operation in which an alarm is automatically given in the event of a failure, is ensured. It is mentioned that rejected parts during press operation as a result of tool wear can arise as a result of quality changes on the workpiece with respect to dimensions or material or as a result of quality of the lubrication. By means of a repeated comparison, in a timed sequence, of the variation of the workpiece-individual stroke/slide force curve with the reference course, rejected parts can be detected automatically and early. In the event of a tolerance range which "accompanies" the reference course being exceeded or undershot, a fault is reported and the machine is deactivated so that, if appropriate, intervention by personnel can occur. The press itself which is monitored in such a way obviously operates, at least until the next failure, with a constant setting of all process parameters.

In another article by D. Bauer, G. Gücker and R. Thor, "computer-supported blank-holding pressure optimizes deep drawing" in the publication Bleche-BänderRohre (Sheet Metal, Strip Metal, Pipes) 5-1990, pages 50 to 54, the authors initially point out that for the deep drawing of fault-free parts it is necessary for the blank-holding force not to be allowed to undershoot a specific minimum value which changes as a function of stroke and not to exceed a specific maximum value which also changes as a function of stroke, the curves for the minimum values and maximum values behaving in a workpiece-dependent fashion. Excessively high blankholding forces lead to fractures on the drawn part, whereas a blank holder which is pressed on too weakly allows folds to arise. The article recommends deviating from the previously widespread variation of the blank-holding force which had a more or less high degree of constancy and using a variation of the blank-holding force against the press stroke which is optimized in dependence on the type of workpiece, it being possible for such a non-constant blank-holding force variation to be made up from several sections of a constant and/or a linearly rising or descending course or from a functionally stipulated course. The desired-value variation for the blank-holding force can be optimized in various aspects according to the cited publication and, depending on the optimization objective, possibly also has a different appearance. For example, the blank-holding force variation can also be optimized with respect to the maximum drawn part quality, in which case it is also possible here again for different considerations, depending on the type of workpiece, to be emphasized, for example freedom from fractures or folds or avoidance of shrink marks. Instead, when optimizing the blank-holding force variation, the design of the drawing process can also be more significant, for example the increase in the acceptable drawing depth with the objective of possibly being able to omit a drawing stage or save on sheet metal or achieve a greater strength of the drawn part. Tribological considerations can also be included in the optimization of the variation of the blank-holding force. The optimized blank-holding force variation, once it has been ascertained for a specific workpiece, is then followed up in a closed-loop controlled fashion during each pressing cycle, the ascertained desired-value curve, with the exception of occasional, subsequent manual improvements, being, however, uniformly maintained.

Despite the use of a variation of the blank-holding force which is optimized to this extent and a corresponding closed-loop control in accordance with this variation, the aforesaid article does not go into details on an automatic detection of errors on the drawn part.

It is already known to monitor stamping processes or stamping tools acoustically (cf., for example, German Patent Document DE-A 3,938,854 or DE-Z Industrie-Anzeiger 17/1991, Pages 40 to 44). In this case, sensors applied to the tool are used to detect signal parameters, in particular the sound amplitude and its range of fluctuation, in temporal correlation with the stamping process, and to compare them with prescribed set values. In stamping processes, the breakage of a punch, for example, can be clearly discerned acoustically; edge chippings or cutting edges that have become blunt can also be detected by comparing the normal sound in the case of a perfect tool with an altered stamping sound. Acoustic monitoring of stamping processes is therefore essentially only a monitoring of the stamping tool, the process control of the stamping process being prescribed essentially completely and finally by the tool design and being virtually incapable of being influenced by machine setting which can be varied in a reciprocating fashion. To this extent, the stamping processes, some of which proceed with cyclic sequences of up to 700 strokes per minute, are not comparable with comparatively slow deep-drawing processes, in which the blank-holding force is slaved to a set characteristic which is to be varied or optimized in a time sequence, as the case may be, during each deep drawing process. Consequently, acoustic monitoring of stamping tools provides no stimulus with regard to automatic process optimization of deep-drawing processes.

An object of the invention is to improve the method of the generic type to the extent that, in the case of non-optimum setting of the process parameters or in the case of a failure which is caused for example by quality changes or lubrication changes on the part of the workpiece, the latter can be detected automatically and early, i.e. while the drawn part is still in the press, and a suitable correction of the set value of the clamping force of the blank holder can become effective immediately, i.e. for the next workpiece and can also be performed automatically.

This object is achieved according to the invention with the method of the generic type means of the following process steps:

before starting up production of drawing parts of a specific type on a specific drawing press and using a specific drawing tool the structure-borne sound of the normal variation in the drawing noise dependent on time or the pressing stroke, that is to say without the risk of the production of "fractures" and without the risk of the production of "folds", is determined by a sound emission analysis of the structure-borne sound caused by the drawn part during the drawing process in the drawing tool, and is stored as a reference sound in the form of data, furthermore, before starting up production of drawn parts of the specific type on the specific drawing press and using the specific drawing tool a reference course of the sound components is respectively determined from this normal drawing noise for the sound components of periodic and of stochastic sound components and stored as data, during the production of drawn parts of this type on the specific drawing press and using the specific drawing tool, the drawn part quality is determined with regard to the criteria of "fractures", "acceptable" and "folds" and the ranges lying therebetween qualitatively are determined automatically and during each working cycle by means of a sound emission analysis of the structure-borne sound caused by the drawn part during the drawing process in the drawing tool, the structure-borne sound signal being examined in each case in a wide frequency spectrum with regard to the simultaneous occurrence of amplitude discontinuities (r) which are abnormal with respect to the reference noise and it being concluded that there is a "fracture" in the case of the occurrence of such spectrally distributed amplitude discontinuities (r), the structure-borne sound signal being examined, furthermore, in each case with regard to the temporal variation in the level of periodic sound components on the one hand, and of stochastic sound components on the other hand, and in the case of a characteristic deviation of the actual-value courses of the actual working cycle from the corresponding reference courses it is concluded that there are "folds", and it being concluded that there is an "acceptable" drawn part in the absence in the sound emission analysis both of the signal characteristics indicating "fractures" and of the signal characteristics indicating "folds" referred to below for short as "damage signals", in order to optimize the clamping force ($F_n$) which can be set at the blank holder, the clamping force ($F_n$) for the following working cycle is changed or maintained uniformly as a function of the detected drawn part quality of a drawn part drawn in a preceding working cycle, specifically in the case of an incipient crack on a previously drawn drawn part—"fractured" drawn part quality—the clamping force ($F_n$) for the new working cycle is lowered with respect to the value set in that case, in the case of a fault-free drawn part—"acceptable" drawn part quality—the clamping force ($F_n$) is maintained uniformly and in the case of folding on a previously drawn drawn part—"folded" drawn part quality—the clamping force ($F_n$) for the new working cycle is increased with respect to the value set in that case.

Before starting up production, the drawing noise for each type of a drawn part that is to be drawn which can be picked up by a vibration sensor that can be applied to the drawing tool, of unambiguously "acceptable" drawn parts is analyzed and a characteristic variation of the amplitude envelope and of the level characteristics of periodic sound components and of stochastic sound components is determined therefor. Limiting data for extreme values or tolerant ranges for curve shapes can be established from these data as set data, dependent on the drawn part, and stored as data. Comparing the corresponding actual data during production with the set data provides the possibility of an automatic fault detection on the drawn part with respect to the damage cases of "fracturing" and "folding" during the drawing process itself. Consequently, corrective interventions can be made promptly as appropriate so that the press can continue to operate in the event of failures and, at most, one faulty part or, in the case of serious failures, possibly two faulty parts are pressed and subsequently acceptable parts are produced again. By means of the automatic fault detection, the method of process optimization which was previously operated, that is to say controlled, manually and under human inspection, becomes a control process which proceeds automatically and in a closed cycle.

In an expedient embodiment of the invention, the time and/or the degree of the damage signal can also be detected within the respective working cycle, in which case the clamping force of the blank holder is changed to a greater extent when a damage signal occurs early or when a stronger damage signal occurs than when a damage signal occurs late or a weaker damage signal occurs.

Further expedient embodiments of the invention consist in the automatic detection of fluctuations of process parameters and/or of quality fluctuations of the semi-finished product, which fluctuations require in each case a corresponding adaption of the blank-holding force in order to achieve optimum process control. Fluctuations of this kind are caused in particular by changes in the material strength of the sheet bars,
the thickness of the sheet metal,
the roughness of the surface of the sheet bars,
the thickness of the lubrication film and
the viscosity of the lubricant.

Other objects, advantages and novel features of the present invention will become apparent from the following detailed description of the invention when considered in conjunction with the accompanying drawings.

BRIEF DESCRIPTION OF THE DRAWINGS

FIGS. 3a to 3d show the time variation in sound amplitude in the case of drawing a specific drawn part with regard to different qualities, specifically "good" in the diagram according to FIG. 3a and increasing fracture lengths in the diagrams according to FIGS. 3b to 3d.

DETAILED DESCRIPTION OF THE PREFERRED EMBODIMENTS

Figure 1:
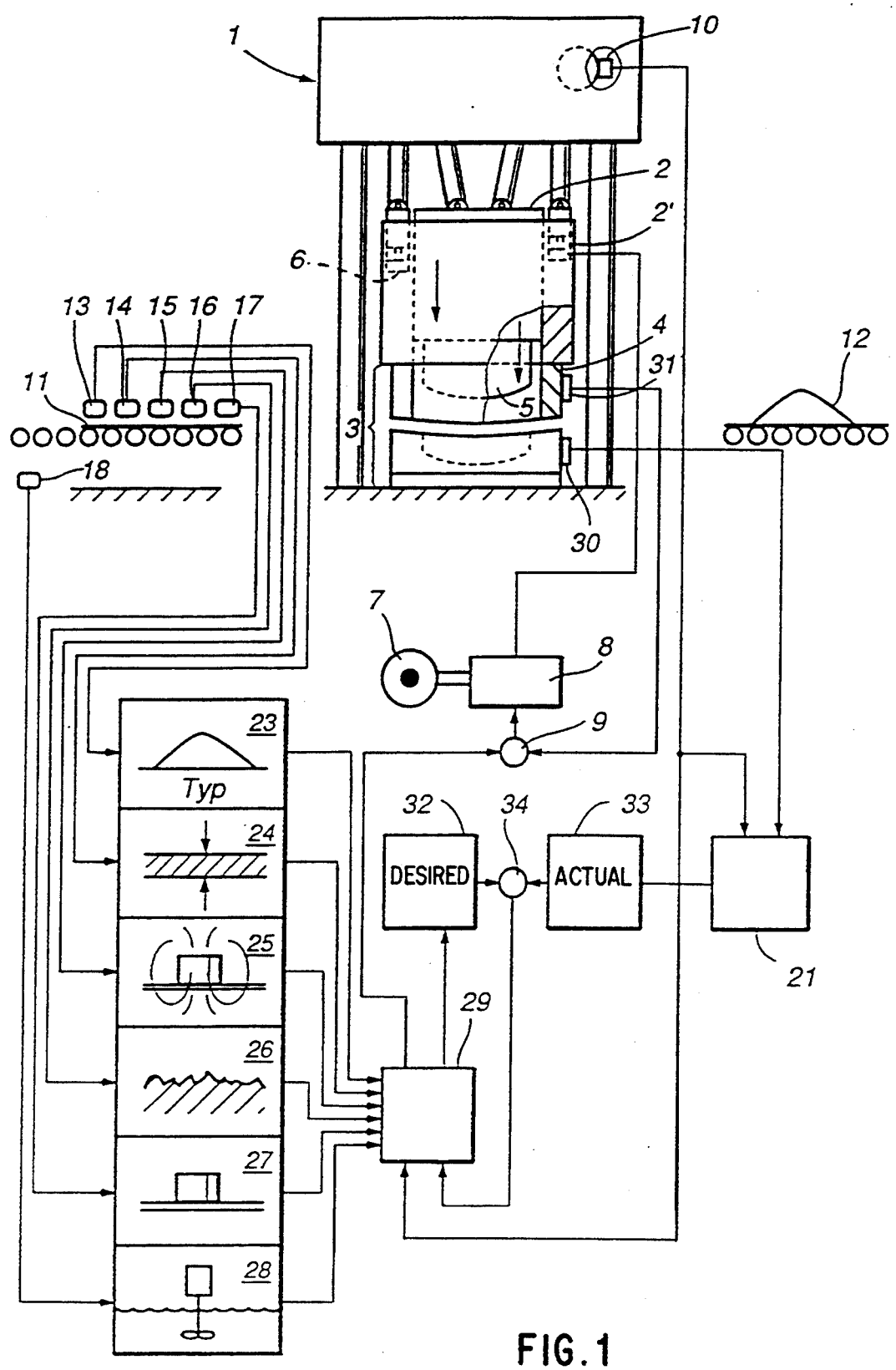
FIG. 1 shows a method diagram for the automatic, iterative process optimization of drawing presses, according to a preferred embodiment of the invention.

In the exemplary embodiment of a method diagram shown in FIG. 1, the drawing press 1 is constructed as a double-acting press in which the lower part of the drawing tool 3, the matrix, which is arranged on the press table, is essentially in one piece, and in which the upper part of the tool 3 is divided into a drawing punch 5 and into a blank holder 4 which comes to bear against the die, the two of which are connected to separate slides 2 and 2', respectively, and are driven by separate strokes. Of course, the present invention can also be applied to single-acting presses or to presses with a hydraulic slide drive. In addition, it can be assumed from the drawing press 1 illustrated in FIG. 1 that its drawing punch is driven in a stroke fashion via a crank drive (not illustrated in greater detail), it being possible to call up the crank angle of the press via an angle sensor 10 and thus to call up unambiguous information relating to the position of the drawing punch in relation to the lower dead-center UT by technical measuring means. At least one force sensor 31 for the continuous detection of the blank-holding force or clamping force is attached to the blank holder 4. This force signal is, like the angle signal of the angle sensor 10, fed into the device (to be explained in even greater detail below) for the automatic iterative process optimization of the drawing process. The blank holder 4 is connected via hydraulic pistons, so-called pressure points 6, to the corresponding connecting rod of the crank drive belonging to it, and these permit the blank holder to be pressed against the bearing surface of the die by means of a hydraulically prescribable force. The pressure points of the blank holder are fed from a pressure source 7 via a proportional valve 8 which can be actuated electrically. It is to be noted here that the pressure point 6 and the associated proportional valve 8 can be provided multiply on the blank holder, for example at each corner, that is to say a total of four can be provided. Accordingly, the associated open-loop or closed-loop control for controlling the clamping force can also be of multi-channel design, however in the method diagram illustrated only a single channel is shown and subsequently explained.

The drawing press 1 operates in a timed sequence, in each case one blank, in the exemplary embodiment illustrated a flat sheet bar 11 of a drawable sheet metal, being inserted into the opened tool 3 during each working cycle, the said tool being clamped in at the edge with a specific clamping force $F_n$ by the blank holder 4 and the drawn part being subsequently drawn between die and drawing punch 5. After the reopening of the tool, the finished drawn part 12 is removed and a new sheet bar 11 is inserted. It is important for the production of acceptable, that is to say fold-free and fracture-free, drawn parts that the blank-holding force $F_n$ lies within a specific range, which is to be explained subsequently in conjunction with the diagram in FIG. 2.

Figure 2:
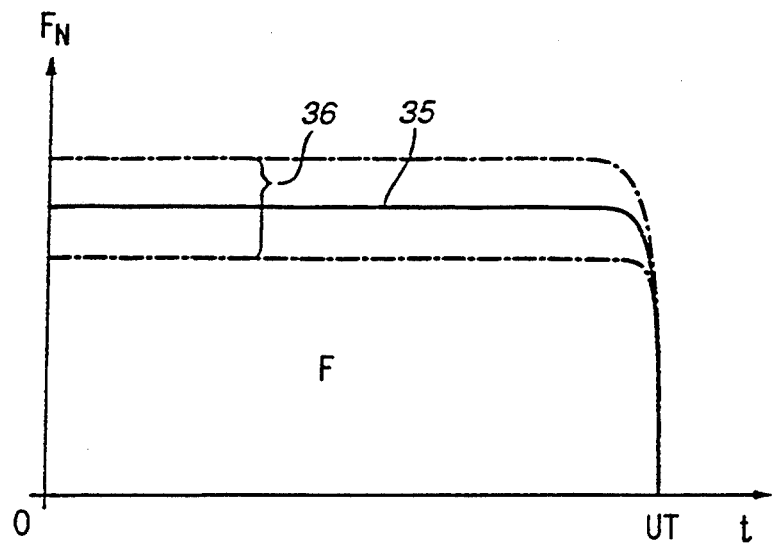
FIG. 2 shows, in diagram form, the ideal variation of the blank-holding force with reference to the example of a blank-holding force which is kept constant with respect to the pressing stroke and shows the desired-value range of the blankholding force lying above and below it.

In FIG. 2, the ideal variation of the blankholding force $F_n$ against the pressing stroke—diagram curve 35—is illustrated for a specific type of drawn part 12. As a rule, this curve has a rectilinear, that is to say, constant shape; it can, however, in some cases, also have a very different shape, depending on the appearance of the drawn part to be produced. Starting from the ideal shape of the blank-holding force, courses above and below it can be permitted. However, with a specific individual piece of a drawn part, the course of the blank-holding force lies too far above the ideal curve 35 so that it must be expected that fractures occur in the drawn part. Conversely, downward deviations of the blank-holding force from the ideal curve can also be permitted up to a certain extent, but are not permitted to be too large, because otherwise the probability of the formation of folds on the drawn part becomes too large. In the diagram according to FIG. 2, a specific hatched area 36 is indicated within which the blank-holding force must stay for individual concrete drawing processes of the respective type of drawn parts, and which may not be exceeded. This range is subsequently referred to as desired-value drawing force range 36. Above it there is the area R in which fractures are to be expected with a very high probability; it can be presumed that folds will arise in the area F lying below the desired-value drawing force range 36. Therefore, in the diagram according to FIG. 2, a tolerable range, for the blank-holding force $F_n$, can be stipulated, which range lies on both sides of the ideal course 35 of the clamping force and can be defined with respect to the fracture area R and the fold area F. The diagram according to FIG. 2 shows an ideal course 35 of the clamping force which remains constant and thus also shows a desired-value clamping force range 36 which extends at a uniform level. However, this depends—as mentioned—only on the respective type of workpiece for which it happens to be optimum that the clamping force is constant over the entire pressing stroke. If, in the case of a different drawn part type, it should be optimum for the clamping force to have a different course, the observation also applies correspondingly for such a part.

It has been observed that the drawing sounds during drawing of faulty parts differ from the drawing sounds during drawing of perfect parts. A systematic investigation of this observation revealed that in the case of drawing sound fractures become noticeable essentially due to spectral broadening, and that folds can be detected by a significant change in the temporal or stroke-dependent variations of the stochastic and/or the periodic sound components by comparison with the corresponding variations during drawing of perfect parts. These findings hold at least on the assumption that the reference variations used for the comparison have been obtained on the same drawing press end with the same drawing tool with which the drawn parts are then also later produced in a monitored way in the production run.

Figure 3A:
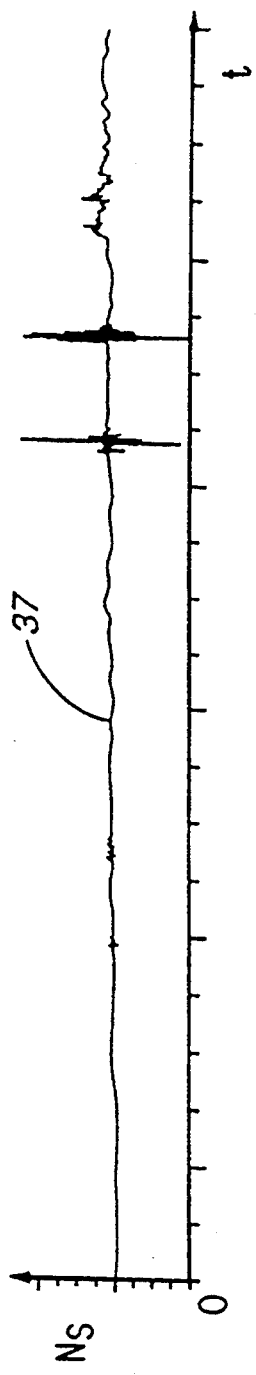
Figure 3B:
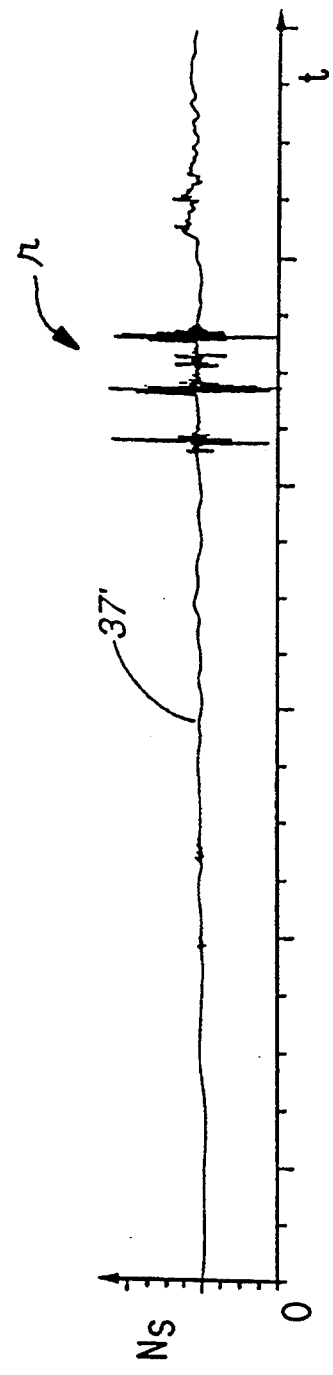

Consequently, before starting up production of drawn parts 12 of a specific type on a specific drawing press 1 and using a specific drawing tool 3, the structure-borne sound caused in the drawing tool during the drawing process is subjected to a sound emission analysis. In this case, for one thing the normal structure-borne sound is determined, that is to say the sound variation which is caused during drawing without the risk of production of "fractures" and without the risk of the production of "folds". This variation in the drawing sound, dependent on time or pressing stroke, is determined with regard to its ideal variation and with regard to the tolerable deviations therefrom and stored as a reference sound in the form of data. Such a reference course 37 is reproduced in FIG. 3a for the amplitude of structure-borne sound which—for the selected workpiece example—shows scarcely any deviation from the zero line over wide ranges of the drawing path, and this indicates in the concrete example a very low drawing sound. Towards the stroke end, shortly before the mounting, denoted by A, of the drawing punch on the die, the reference course 37 shows for the amplitude an amplitude peak which is, however, to be denoted as "normal" for the selected example. The comparison of this reference course with the diagram lines according to FIGS. 3b to 3d, which were obtained during drawing with an excessively high blankholding force, reveals that the fractures produced on the drawing parts are distinguished by at least one additional amplitude peak denoted by r. The three sound recordings according to FIGS. 3b to 3d were obtained for drawing with an increased blank-holding force in each case, so that the fractures provoked turned out in each case to be longer than in the preceding experiment. In the respective sound recordings, the fracture-indicating peaks r are situated earlier in time the higher the blank-holding force was set, and thus the longer also the fracture turned out to be. Although a fracture-indicating sound signal does not turn out in all cases as clearly as in the selected example, it can be detected clearly even in less favorable cases by using measurement techniques.

Figure 4A:
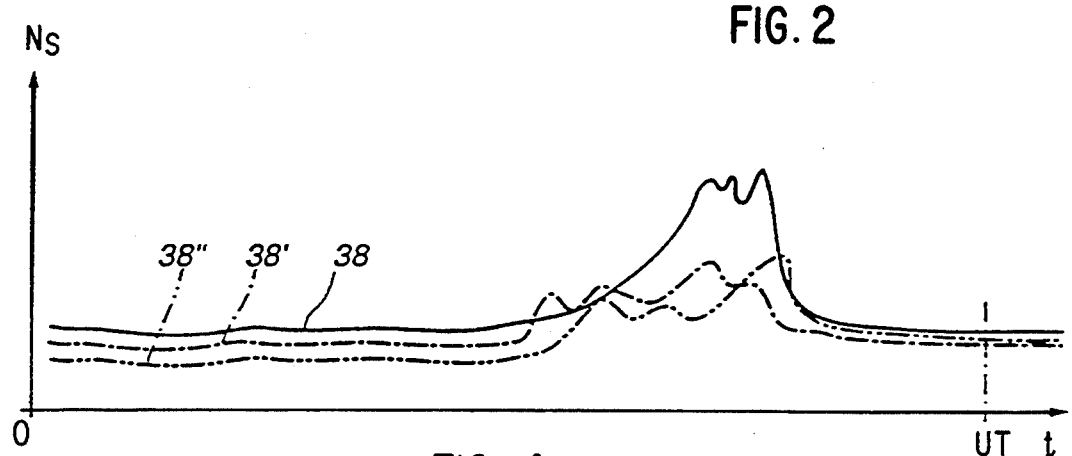
FIGS. 4a and 4b show the time variation in the acoustic power of stochastic (FIG. 4a) and, respectively, periodic (FIG. 4b) sound components from the drawing sound of a further drawn part with reference to different qualities, the continuous diagram lines corresponding to good parts and the two other diagram lines corresponding to drawn parts which are more or less strongly folded.
Figure 4B:
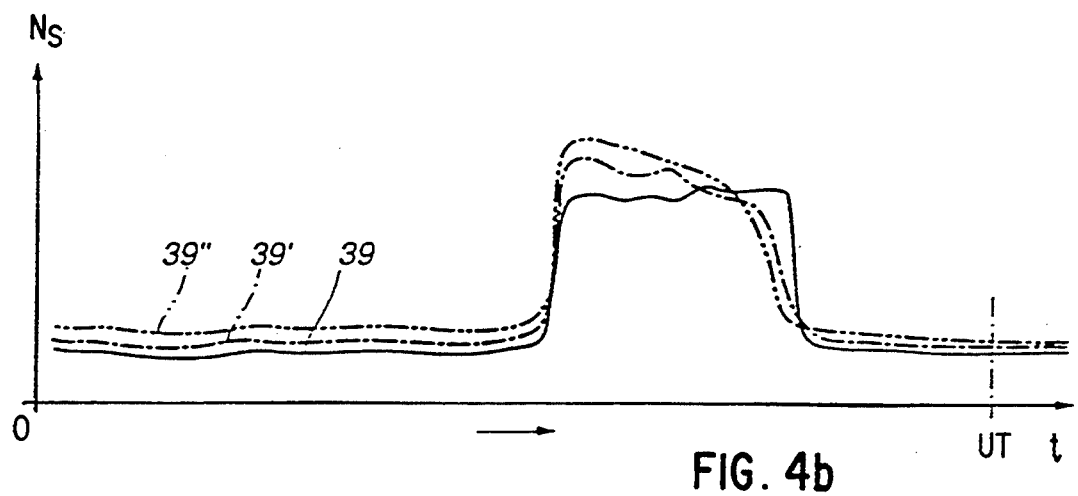

On the other hand, such a normal drawing sound obtained for a specific drawn part is used, likewise before starting up production, respectively to determine a reference course for the sound components of periodic and of stochastic sound components, which are stored as data. FIGS. 4a and 4b show in full lines the reference courses 38 and 39, respectively, of the stochastic sound components as acoustic power $N_s$ (FIG. 4a, diagram curve 38), and for the periodic sound components (FIG. 4b, diagram curve 39), plotted against time for a specific drawn part. Due to the clarity with which by comparison with the respective reference courses the fractures on the one hand and the folds on the other hand are shown, different drawn parts were selected for the diagram curves shown here for sound amplitude, on the one hand, (FIGS. 3a to 3d) and for the stochastic and periodic sound components, on the other hand (FIGS. 4a and 4b). In the concrete example of the diagram curves according to FIGS. 4a and 4b, it is seen that the two sound components addressed remain approximately constant over large distances of the drawing path, and are situated at a low level. The reference courses 38 and 39, respectively, adopt a significantly different shape only in a central region of the drawing path, where the drawing sound is louder. Also plotted in the diagrams of FIGS. 4a and 4b in dots and dashes for the purpose of comparison are corresponding courses which were obtained with an excessively low blank-holding force, with the result that a formation of folds was provoked on the corresponding drawn parts. The diagram curves 38' and 39' with in each case only one point between two adjacent dashes were obtained with a moderately reduced blank-holding force, and consequently the drawn parts showed only a slight formation of folds; the diagram curves 38" and 39" (two points between the dashes) correspond to a greatly reduced blank-holding force and a strong formation of folds. It may be seen that in the case of drawing folded parts both the stochastic and periodic sound components produce a significantly different course than in the case of drawing perfect parts, to be precise particularly in the period in which the drawing sound is louder. The difference between the reference course and the actual curve of a particular faulty part would become even clearer through forming a quotient.

During the production of drawn parts of a specific type for which reference courses have been determined on the same drawing press and using the same drawing tool as used for the production, a sound emission analysis is carried out for the structure-borne sound caused by the drawn part during the drawing process in the drawing tool, and a comparison with the reference courses is carried out. Consequently, the quality of the drawn part is automatically determined continuously, that is to say in each working cycle, with regard to the criteria of "fracture", "acceptable" and "folds". Specifically, the structure-borne sound signal 38', 38", 38''' is examined in each case in the wide frequency spectrum with regard to the simultaneous occurrence of amplitude discontinuities r which are abnormal with respect to the reference noise. For the case of the occurrence of such spectrally broadened amplitude discontinuities, it can be concluded that there are "fractures"; otherwise it can be assumed that the drawn part is fracture-free. The structure-borne sound signal is, furthermore, examined in each case with regard to the temporal variation in the periodic and the stochastic sound components. Given a characteristic deviation of the actual courses, obtained from the actual working cycle, from the corresponding reference courses, it is concluded that there are "folds", and given agreement between the actual courses and the reference courses, it can be said with adequate reliability that the drawn part produced is fold-free.

Therefore, after it can be determined, with reference to the actual respective variation in the drawing sound or the variation in the level of the stochastic and the periodic sound components against the pressing stroke by comparing with the corresponding desired curves determined for the respective drawn part, whether the manufactured drawn part is acceptable or has fractures or folds, it can be decided whether the clamping force is to be maintained at the same level for the next pressing cycle, to be decreased or increased. The present invention exploits this consideration.

In order to optimize the clamping force $F_n$ which can be adjusted on the blank holder 4, as a function of the detected drawn part quality of the drawn part drawn in the previous working cycle, the clamping force for the next working cycle is varied or maintained constant, specifically in the case of an incipient crack on a previously drawn drawn part—drawn part quality of "fracture"—the clamping force is lowered with respect to the value set in this case for the new working cycle, in the case of a perfect drawn part—drawn part quality "acceptable"—the clamping force is held constant, and in the case of folding on a previously drawn drawn part—drawn part quality of "folding"—the clamping force is increased with respect to the value set in this case for the new working cycle.

For this purpose, a function memory 32 is provided for the reference drawing sound 37 and for the reference courses 38 and 39 of the stochastic and periodic sound components, respectively. In addition, a function memory 33 is installed for the respective actual-value drawing force sound 37' or 37'' or 37''' and for the actual-value courses 38' and 39' or 38'' and 39'' of the stochastic and periodic sound components, respectively. These actual-value courses are automatically determined in a sound analyzer 21 connected upstream of the function memory 33 and into which apart from the signal, applied to the die, of the vibration sensor 30 for the drawing sound there is also fed the signal of the angle sensor 10 for the crankshaft angle. In a comparator 34, a comparison can be carried out between the different reference courses on the one hand and the respectively corresponding actual-value courses on the other. If this comparison gives positive results, i.e., if the actual-value courses correspond with the reference courses within a certain tolerance range, the next pressing stroke is carried out with the same clamping force or with the clamping force course with which the last drawn part is also drawn. If, on the other hand, the result of the desired-value/actual-value comparison of the drawing sounds is that a fracture indicating peak r can be detected at some point of the pressing stroke, not only is the respective part ejected from the further production process, but the blankholding force is also automatically reduced for the next pressing stroke. In the event that it should be possible during the comparison of the level courses of the stochastic and the periodic sound components, respectively to detect a deviation in the actual-value course with respect to the reference course of the desired-value drawing force range at some point of the pressing stroke, during the next pressing stroke a higher blank-holding force is thus automatically set.

A computer 29 which feeds appropriate data into the function memory 32 for the reference drawing sound and the reference level courses from a relatively large, preferably separate file is provided as an important component of such a control device. As long as the quality of the sheet bars 11 and the quality of the sheet bar lubrication remains unchanged, the data for the reference drawing sound and for the reference level courses set in the function memory 32 are also unchanged. The computer 29 also supplies to the point 9 of the desired-value/actual-value comparison for the blankholding force $F_n$ the respective desired value for the blank-holding force which is constant against the pressing stroke in the example shown in FIG. 2. In other drawn parts with a course of the blank-holding force which is optimally not constant, a correspondingly variable desired-value would be fed into the comparison point 9 as a function of the pressing stroke. Depending on the result of the desired-value/actual-value comparison between the desired and actual clamping force, the clamping force is increased or reduced via the proportional valve 8 so that the desired course of the clamping force can be followed in a controlled fashion.

The computer 29 is also provided with the result of the desired-value/actual-value comparison between the actual-value drawing sound and the actual-value level courses on the one hand and the desired-value drawing sound and the actual-value level courses, respectively, on the other. Depending on the result of this comparison, as stated, the same value as previously is fed from the computer 29 into the comparison point 9 as a new desired-value for the blank-holding force or, if appropriate, even a changed desired-value for the subsequent pressing stroke. This computer therefore stipulates for each individual pressing stroke in each case the desired-value or the desired-value course for the blank-holding force according to which the said force is to be adjusted; in addition, the computer 29 supplies the data for the desired-value drawing sound and the desired-value level courses, which it feeds into the function memory 32 and, if required, also changes from one pressing stroke to the next.

In the desired-value/actual-value comparison between the reference courses on the one hand and the corresponding actual-value courses on the other, if appropriate not only is the fact of a deviation and the direction of the deviation detected but also the time of the deviation within the pressing stroke and the size of the deviation are detected. In the case of a negative desired-value/actual-value comparison, this information permits the computer 29 to react selectively as a function of the instant and/or the extent of the deviation between the two—damage signal. When a damage signal occurs early, the blank-holding force for the next pressing stroke changes to e greater extent than in the case of a later damage signal. In the same way, a very strong damage signal also leads to a higher degree of change of the blank-holding force, and vice versa. As a result, in the case of a setting of the blank-holding force which is highly erroneous, optimum setting can be achieved in few iteration steps, ideally with only one step.

Previously, it was assumed that the sheet bar quality and the quality of the lubrication remain unchanged. Given this assumption, corresponding failures could still at most originate from the press itself. It would be possible to intercept or compensate failures of this kind through use of the previously described system. Workpiece-side failures which are due to quality changes in the sheet bar or its lubrication would, however, have to be detected promptly at the sheet bar and fed into the open-loop or closed-loop control system. For this reason, a plurality of sensors, with which the properties of the sheet bar or its lubrication which are relevant for a uniform drawing result can be detected using measuring technology, are provided in the area of the sheet bar. Firstly, an input point 13 for the respective type of workpiece is provided; it is coupled to a corresponding data processing device 23 which provides a base function for the optimum level course of the stochastic and the periodic sound components and the desired-value drawing sound as well as a base function for the ideal course 35 of the blank-holding force and the desired-value clamping force range 36 to the computer 29. This data is stored in the function part 23 of the data processing device for the type of workpiece and is called up appropriately. Furthermore, a sensor 14 for the detection of the thickness of the sheet metal of the sheet bar 11 is provided, with which sensor 14 fluctuations in the thickness of the sheet bar can be detected. The corresponding signals are fed to a further function part 24 for the data processing in relation to the thickness of the sheet metal; the said function part 24 contains correction factors or correction algorithms which are to be taken into account in the case of dimensional deviations with respect to a nominal value of the thickness of the sheet bar; these correction factors or algorithms are also passed on to the computer 29. By means of a further sensor 15, the quality of the material of the sheet bar can be detected. This can be for example an inductively operating sensor which measures the magnetic permeability of the sheet metal very sensitively and makes conclusions regarding different degrees of material strength from changes in this value. The corresponding signals are also passed on to a function block 25 for the data processing in relation to the material quality which also feeds the computer 29 with appropriate correction values or correction algorithms in accordance with the deviation with respect to a standard value. Furthermore, the surface quality, in particular the roughness of the sheet bar, is significant and can be detected by means of a sensor 16 which operates for example in an optical fashion. Corresponding measurement values are also passed on to the associated function block 26 for the data processing for roughness, which function block 26 itself passes on correction values or algorithms to the computer 29 if the measured roughness deviates in one direction or another with respect to a standard value. Finally, the type of lubrication of the sheet bar is also important for a uniform drawing result. In this context, the thickness of the lubrication film, which can be measured by means of a sensor 17 which operates for example capacitively. The connected function block 27 for the data processing of the thickness of the lubrication film also feeds the computer 29 with corresponding correction values or algorithms in the event of a deviation of the thickness of the lubrication film with respect to a standard value. The viscosity of the lubricant used is continuously detected with the sensor 18; the correspondingly connected function block 28 for the data processing with respect to the viscosity of the lubricant is also connected to the computer 29.

By virtue of the continuous quality monitoring of the sheet bar and of the lubrication with respect to the mentioned properties and the corresponding data processing, the computer 29 is able to calculate in advance a respective data set, adapted to the changed sheet bar-side conditions, for the position and/or the variation in the desired-value drawing force range 36 and the desired-value course 35 of the blank-holding force for the next pressing cycle. In fact, in the event that the material strength is increased with respect to a standard value, the blank-holding force must be greater than normal. It is similar with the thickness of the sheet metal; in the case of a thicker sheet metal, the blank holder must also be pressed on more strongly than in the case of a less thick metal sheet. In the case of the roughness of the surface of the sheet bar the opposite is true; the rougher the surface, the smaller the blank-holding force must be in order to obtain the trend of identical drawing qualities. The trend for the thickness of the lubrication film behaves with an opposite effect; the thicker the lubrication film, the greater the blank-holding force which is required in order to obtain drawing results of the same kind. It is also similar with the viscosity of the lubricant; with a viscous lubricant, the trend must be for the edge of the sheet bar to be clamped more strongly than in the case of a low-viscosity lubricant.

Apart from respectively determining in advance the desired-value drawing force range 36 and the desired-value course 35 of the blank-holding force for the next pressing cycle, the computer 29 also further determines, if appropriate, whether a reference drawing sound modified with respect to the previous pressing cycle and/or a changed reference course of the stochastic and/or the periodic sound component of the relevant desired-value/actual-value comparison is to be taken as the basis and therefore to be set in the function memory 32.

When using an adaptive computer, the extremely different influences and the degree to which they are to be taken into account in practice can be optimized automatically.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method of manufacturing parts in a drawing press of the type where a part blank is inserted into a press working tool for each cycle of the drawing press, said tool including a die, punch and blank holder with clamping in of the part by the blank holder with a specific clamping force and the part being subsequently drawn between die and punch, said method comprising operating with the following sequential steps performed for manufacturing a plurality of parts:

conducting sound emission analyses for a given press tool and blank part to be drawn to determine production sound emissions including periodic and stochastic sound components which are stored as part sound reference data including good part sound reference data, unacceptable fracture part sound reference data and unacceptable fold part sound reference data, subsequently producing a drawn part in a press working cycle while analyzing sound emission of the press and comparing same to the stored part sound reference data, and automatically and continuously sequentially producing subsequent drawn parts in subsequent press working cycles with adjustment of the clamping force to an optimum blank-holding force in the event the actual sound emission of the press during production of the previous part during the immediately preceding working cycle deviates from the good part sound reference data, with lowering of the clamping force in the event the actual sound emission corresponds to unacceptable fracture parts sound reference data and within increase of the clamping force in the event the actual sound emission corresponds to unacceptable fold part sound reference data.

2. Method according to claim 1, wherein the material strength of each incoming part blank is also detected, the clamping force of the blank holder being set higher in the case of high strength than in the case of low strength.

3. Method according to claim 2, wherein the sheet metal thickness of the part blank is also detected, the clamping force of the blank holder being set higher in the case of greater sheet metal thickness than in the case of lesser sheet metal thickness.

4. Method according to claim 3, wherein the roughness of the surface of the part blank is also detected, the clamping force of the blank holder being set lower in the case of greater roughness than in the case of lesser roughness.

5. Method according to claim 4, wherein each part blank is provided with a lubricating film before insertion into the drawing tool, and wherein the thickness of the lubricating film is also detected, the clamping force of the blank holder being set higher in the case of greater lubricating film thickness than in the case of lesser lubricating film thickness.

6. Method according to claim 5, and wherein the viscosity of the lubricant is also continuously detected, the clamping force of the blank holder being set higher in the case of a more viscous lubricant than in the case of less viscous lubricant.

7. Method according to claim 6, wherein the optimum blank-holding force for the part blank which is to be newly inserted into the drawing press is calculated in advance on the basis of previous pressing cycles and from the measurement parameters, detected on a sheet bar which is to be newly inserted into the drawing press, the said measuring parameters relating to material strength, sheet metal thickness, roughness, thickness of lubricating film and/or viscosity.

8. Method according to claim 1, wherein the sheet metal thickness of each incoming part blank also detected, the clamping force of the blank holder being set higher in the case of greater sheet metal thickness than in the case of lesser sheet metal thickness.

9. Method according to claim 1, wherein the roughness of the surface of each incoming part blank is also detected, the clamping force of the blank holder being set lower in the case of greater roughness than in the case of lesser roughness.

10. Method according to claim 1, wherein each part blank is provided with a lubricating film before insertion into the drawing tool, and wherein the thickness of the lubricating film is also detected, the clamping force of the blank holder being set higher in the case of greater lubricating film thickness than in the case of lesser lubricating film thickness.

11. Method according to claim 1, wherein each part blank is provided with a film of a lubricant before insertion into the drawing tool, and wherein the viscosity of the lubricant is also continuously detected, the clamping force of the blank holder being set higher in the case of a more viscous lubricant than in the case of less viscous lubricant.

12. Method according to claim 1, wherein the optimum blank-holding force for the part blank which is to be newly inserted into the drawing press is calculated in advance on the basis of previous pressing cycles and from the measurement parameters, detected on a part blank which is to be newly inserted into the drawing press, the said measuring parameters relating to material strength, sheet metal thickness, roughness, thickness of lubricating film and/or viscosity.

13. A method according to claim 1, wherein said producing subsequent drawn parts includes adjustment of the acceptable sound reference data in response to a monitored condition of at least one of (i) a quality characteristic of incoming part blanks to be drawn in subsequent press working cycles and (ii) the viscosity of lubricant applied to the incoming part blanks being processed.

14. Method according to claim 1, wherein said conducting sound emission analyses includes determining a sound pattern as a function of time over the press working cycle, said sound patterns serving as the stored part sound reference data.

15. Method according to claim 14, wherein said good part sound reference data includes a range of good part sound patterns, wherein said unacceptable fracture part sound reference data includes a range of unacceptable fracture part sound patterns above the range of good part sound patterns, and wherein said unacceptable fold part sound reference data includes a range of unacceptable fold part sound patterns below the range of good part sound patterns.

16. Method according to claim 15, wherein said analyzing of sound emission of the press during production of drawn parts in a press working cycle includes determining at least one of the time and the degree of deviation of the actual sound pattern from the range of good part sound patterns, and wherein said control of the clamping force in a subsequent press working cycle includes varying the degree of clamping force change as a function of said degree of deviation from the actual sound pattern, with greater changes to the clamping force when the unacceptable part sound signal occurs earlier in the press cycle and when a greater deviation from the good part sound pattern occurs than when a weaker deviation occurs.

17. A drawing press of the type where a part blank is inserted into a press working tool for each cycle of the drawing press, said tool including a die, punch and blank holder with clamping in of the part by the blank holder with a specific clamping force and the part being subsequently drawn between die and punch, said press comprising:

means for conducting sound emission analyses for a given press tool and blank part to be drawn to determine production sound emissions including periodic and stochastic sound components which are stored as part sound reference data including good part sound reference data, unacceptable fracture part sound reference data and unacceptable fold part sound reference data, means for subsequently producing a drawn part in a press working cycle while analyzing sound emission of the press and comparing same to the stored part sound reference data, and means for automatically and continuously sequentially producing subsequent drawn parts in subsequent press working cycles with adjustment of the clamping force to an optimum blank-holding force in the event the actual sound emission of the press during production of the previous part during the immediately preceding working cycle deviates from the good part sound reference data, with lowering of the clamping force in the event the actual sound emission corresponds to unacceptable fracture parts sound reference data and within increase of the clamping force in the event the actual sound emission corresponds to unacceptable fold part sound reference data.

18. A drawing press according to claim 17, wherein means are provided for calculating the optimum blank-holding force in advance on the basis of the prior pressing cycle sound pattern and at least one measured physical parameter of a next part to be inserted into the drawing part.

19. A drawing press according to claim 18, wherein said at least one measured physical parameters include at least one of the part material strength sheet metal thickness, roughness, thickness of lubricating film, and viscosity of lubricating film.

* * * * *